United States Patent [19]

Mattei et al.

[11] Patent Number: 4,532,929
[45] Date of Patent: Aug. 6, 1985

[54] DRY COATING OF SURGICAL FILAMENTS

[75] Inventors: Frank V. Mattei, Piscataway; Donald W. Regula, Flagtown, both of N.J.

[73] Assignee: Ethicon, Inc., Somerville, N.J.

[21] Appl. No.: 633,759

[22] Filed: Jul. 23, 1984

[51] Int. Cl.³ .............................................. A61L 17/00
[52] U.S. Cl. .................................... 128/335.5; 427/2; 428/263; 428/378
[58] Field of Search ........................... 128/335, 335.5; 428/263, 378; 427/2

[56] References Cited

U.S. PATENT DOCUMENTS

| | | | |
|---|---|---|---|
| 3,478,140 | 11/1969 | Kronenthal et al. | 128/335.5 |
| 4,027,676 | 6/1977 | Mattei | 128/335.5 |
| 4,047,533 | 9/1977 | Perciaccante et al. | 128/335.5 |
| 4,105,034 | 8/1978 | Shalaby et al. | 128/335.5 |
| 4,201,216 | 5/1980 | Mattei | 128/335.5 |

*Primary Examiner*—Jacqueline V. Howard
*Attorney, Agent, or Firm*—Charles J. Metz

[57] ABSTRACT

Braided or monofilament surgical filaments are coated with dry, powdered, substantially water-insoluble, absorbable salt of a $C_6$ or higher fatty acid, such as calcium stearate.

20 Claims, No Drawings

DRY COATING OF SURGICAL FILAMENTS

TECHNICAL FIELD

This invention relates to a dry, absorbable composition useful as a coating and lubricating finish for surgical filaments, and to a method for using said composition. More particularly, this invention relates to a means for improving the tie-down properties of absorbable and non-absorbable monofilament surgical filaments as well as multifilament surgical filaments by coating them with a dry, absorbable lubricating composition.

BACKGROUND ART

Suture materials and other surgical filaments such as ligatures are generally classified as either absorbable or non-absorbable, with each type of suture material being preferred for certain applications. Absorbable suture materials are preferred for internal wound repair in which the sewn tissues will hold together without suture reinforcement after healing and in which a nonabsorbed suture may promote tissue irritation or other adverse bodily reaction over an extended period of time. Suture materials are considered to be absorbable if they disappear from the sewn tissue within about a year after surgery, but many absorbable suture materials disappear within shorter periods.

The earliest available absorbable suture materials were surgical gut and extruded collagenous materials. More recently, absorbable sutures derived from synthetic polymers have been developed which are strong, dimensionally uniform, and storage stable in the dry state. Typical of such polymers are lactide homopolymers and copolymers of lactide and glycolide such as those disclosed in U.S. Pat. No. 3,636,956, and glycolide homopolymers such as those disclosed in U.S. Pat. No. 3,565,869.

Monofilament synthetic absorbable suture materials are generally stiffer than their multifilament surgical gut or collagen counterparts, and synthetic absorbable sutures are therefore usually employed in a multifilament, braided construction in order to provide the suture with the desired degree of softness and flexibility. Such multifilament sutures exhibit a certain degree of undesirable roughness or "grabbiness" in what has been termed their "tie-down" performance, i.e., the ease or difficulty of sliding a knot down the suture into place, or the ease of snugging a square knot in place.

Multifilament nonabsorbable sutures such as braided sutures of polyethylene terephthalate, for example, can be improved with respect to tie-down performance by coating the external surface of the suture with solid particles of polytetrafluorethylene and a binder resin as disclosed in U.S. Pat. No. 3,527,650. This procedure, however, is undesirable as applied to absorbable sutures because polytetrafluoroethylene is nonabsorbable and sutures coated therewith would leave a polymer residue in the sewn tissue, after the suture had been absorbed.

Multifilament, nonabsorbable sutures can also be improved with respect to tie-down performance by coating them with a linear polyester having a molecular weight between about 1,000 and about 15,000 and at least two carbon atoms between the ester linkages in the polymer chain as disclosed in U.S. Pat. No. 3,942,532.

U.S. Pat. No. 3,297,033 discloses that the synthetic absorbable sutures described therein may be coated with conventional suture coating materials such as a silicone or beeswax in order to modify the handling or absorption rate of the sutures. These coating materials are not readily absorbable, however, and will accordingly leave an undesirable residue in the tissue after the suture itself is absorbed.

Many other compounds have been proposed as treating agents to improve the lubricity and handling of both natural and synthetic filaments. U.S. Pat. No. 3,896,841 describes the treatment of collagen sutures with a hygroscopic agent and lubricant to provide a suture which permanently retains at least 10 percent by weight moisture. Sutures so treated are reported to have increased suppleness and reduced drag when passing through tissue. Fatty compounds and derivatives of fatty compounds are suggested as useful lubricating agents for such collagen sutures.

U.S. Pat. No. 3,982,543 discloses that multifilament, absorbable sutures may be lubricated/coated with a copolymer of lactide and glycolide in order to reduce the capillarity of the suture, and that sutures so treated are reported to have improved run down.

Because of the nature of surgical procedures, sutures and ligatures are generally exposed to body fluids or passes one or more times through moist tissue before tying, and an effective suture coating composition ideally provides wet tie-down characteristics substantially equivalent to those of the dry suture.

U.S. Pat. No. 4,143,423 discloses coating surgical appliances with a gloving agent or lubricant comprising a water soluble nontoxic alkali metal compound such as sodium bicarbonate. The compound may be coated as a powder by dusting or from an aqueous solution. Water soluble compounds would not, however, be suitable as lubricants for surgical sutures due to the nature of surgical procedures. Thus, the lubricant powders would be dissolved prematurely.

U.S. Pat. No. 4,201,216, issued May 6, 1980, to Frank V. Mattei, discloses as a coating for sutures, particularly synthetic absorbable multifilament sutures, an absorbable composition comprising a film-forming polymer and a substantially water-insoluble salt of a $C_6$ or a higher fatty acid. The coating is preferably applied to the suture from a solvent solution to provide a final coating add-on of from about 2 to 10 percent by weight of the sutures. In accordance with the teachings of said U.S. Pat. No. 4,201,216, the film-forming polymer is preferably a copolymer of lactide and glycolide, while the fatty acid salt is preferably a calcium salt of a $C_6$ to $C_{22}$ fatty acid. The ratio of polymer to fatty acid salt in the coating composition may be within the range of about 1:4 to 4:1 parts by weight. The coating is wholly absorbable and is particularly useful for improving the dry and wet tie-down smoothness of braided sutures prepared from homopolymers and copolymers of lactide and glycolide, and other absorbable polymers. The patent discloses that where the compositions of the suture and the film former are identical, and in other instances where the suture material may be subject to some surface dissolution and/or surface swelling or softening by reason of the action of the film former solvent thereon, there may be a gradual transition between the substrate composition and the coating composition rather than a sharp interface between them. There may also be some weakening of the suture accompanying the application of such coating compositions.

It is an object of this invention to provide an improved method for coating monofilament sutures, as well as multi-filament sutures of braided, twisted or covered construction, with a coating that improves the tie-down properties of such monofilament or multifilament sutures. It is a further object of this invention to provide a wholly absorbable coated synthetic monofilament or multifilament suture having improved and substantially equal dry and wet knot tie-down properties. It is yet a further object of this invention to provide such a wholly absorbable coated synthetic monofilament or multifilament suture having improved tie-down properties at least as desirable as those of sutures prepared in accordance with the teaching of U.S. Pat. No. 4,201,216, but having a substantially lower coating weight than that of the sutures of said U.S. Pat. No. 4,201,216, thus tie-down is improved by the minimal application of a safe material, such application being accomplished without using any organic solvents. The appearance and other esthetic attributes of the suture are only minimally affected, if at all, by the low level of add-on of the dry lubricating composition of the invention.

DETAILED DESCRIPTION OF THE INVENTION

In accordance with the invention, there is provided as a coating for surgical filaments such as sutures, and ligatures, particularly synthetic absorbable monofilament surgical filaments, an absorbable composition comprising a dry, finely powdered, substantially water insoluble salt of a $C_6$ or higher fatty acid. The coating may be applied on continuous lengths of monofilament or braid, using a series of powdered soft brushes followed by clean, soft wiping brushes to remove excess coating powder, or using other powder coating techniques that are known to the art, to provide a final coating add-on of below about 0.25 percent, and preferably below about 0.15 percent, by weight of the filament. The coating may also be applied to the filament manually by pulling the filament through fingers that had been powdered with the coating salt, e.g., calcium stearate, followed by pulling several times through clean fingers to remove any visible signs of the coating powder.

The fatty acid salt is preferably a calcium salt of a $C_6$ to $C_{22}$ fatty acid. The coating is particularly useful for improving the dry and wet tie-down smoothness of monofilament sutures, such as those prepared from homopolymers and copolymers of p-dioxanone, polyolefins such as polypropylene, certain polyesters, and the like, as well as braided sutures prepared from homopolymers and copolymers of lactide or glycolide and other absorbable polymers, polyethylene terephthalate, silk, and the like.

The fatty acid salts useful in the coating powder compositions of the invention include the calcium, magnesium, barium, aluminum, and zinc salts of $C_6$ and higher fatty acids, particularly those having from about 12 to 22 carbon atoms, and mixtures thereof. The calcium salts of stearic, palmitic and oleic acids are particularly preferred for use in the invention. Mixtures of these salts may offer advantages in certain applications.

The amount of coating composition applied to the suture, or the coating add-on, will vary depending upon the construction of the suture, e.g., the number of filaments and tightness of braid or twist. In general, the coating composition applied to a suture will constitute up to about 0.25 percent by weight of the coated suture, and preferably up to about 0.15 percent by weight of the suture. As a practical matter, and for reasons of economy and general performance, it is generally preferred to apply the minimum amount of coating composition consistent with good tie-down performance, and this level of add-on is readily determined experimentally for any particular suture-coating system. Usually, the add-on will be at least about 0.02 weight percent, based on suture weight.

The improvement in tie-down properties imparted to sutures and ligatures may be determined semiquantitatively and subjectively by comparing the tie-down smoothness of coated and uncoated filaments during the act of tying down a single throw knot. Such comparisons are preferably made on both wet and dry filaments since many filaments materials have different tie-down properties when tested wet or dry. Tie-down roughness is graded from 0 to 10, with 0 being comparable to a rough filament and 10 indicating no detectable roughness.

Tie-down properties are evaluated dry after the strands of suture or ligature have been conditioned for at least 2 days in a vacuum drying oven at room temperature and 100 microns absolute pressure, and wet after being immersed in water at 25° C. for 1 minute. Values above 4 are considered acceptable, while values of 7 or higher are comparable to conventional silicone coated silk and are considered fully satisfactory.

The tie-down roughness test is carried out as follows:

The calibration standards for the test are uncoated poly(glycolide-co-lactide) braid, size 2/0, which is arbitrarily assigned a 0 rating, and size 2/0 braided poly(ethylene terephthalate) having a coating of polytetrafluoroethylene, which is assigned a 10 rating. A 24–36 inch strand of the material being tested is looped under a stationary bar, and a single throw know (overhand knot) is formed between the two free ends, near the ends. The two ends are grasped firmly in the hands and the ends are arranged so that the knot has its loops evenly spread out. Using 1–2 pounds of tension, the knot is caused to slide down at a moderate rate, with an even pull, until it comes to rest on the bar. After calibrating the strands for some 10–15 minutes with the two standards, the smoothness of tie-down is judged for the test samples, using the 0–10 scale. Usually, some 3–5 tie-downs are done on each strand, and about 4 strands are done per sample. For wet tie-down, the test is carried out immediately upon removal from the water. Only about 3 to 4 wet tie-downs are done on each strand, since the strand begins to dry out immediately upon removal from the water, and after 3 or 4 tests, is no longer wet. An average is taken of all the evaluations. While the test is subjective, and obviously operator-dependent, experiences has shown that different persons carrying out the test will get about the same results (i.e., the trends and differences between samples will be the same), even though the specific numbers obtained may not be exactly the same.

The following examples are provided to further illustrate and demonstrate the method and product of the invention. Unless otherwise stated, all parts and percentages are by weight.

EXAMPLE 1

Dry, powdered (100 percent smaller than 21 microns, 50 percent smaller than 8.5 microns) calcium stearate (in the form of a commercial food grade product consisting of about ⅓ $C_{16}$ and ⅔ $C_{18}$ fatty acid, with small amounts of $C_{14}$ and $C_{22}$ fatty acids) was applied as follows to size 1 dyed poly-p-dioxanone monofilament which had been scoured in acetone for three hours and then dried. The operator's fingers were powdered with the calcium stearate and the strands then individually pulled through the fingers 4–8 times so as to obtain a thorough and intimate coating. After removing the stearate from the fingers, the strands were pulled through clean fingers several more times to remove any visible signs of stearate.

EXAMPLE 2

The foregoing procedure was repeated using the monofilaments and fatty acid salt coating powders identified in Table I. The tie-down properties of the strands were then evaluated using the heretofore described semi-quantitative smoothness-of-tie-down tests, with the results set forth in Table I. The sterilized samples were sterilized either by ethylene oxide (EO) or by gamma irradiation from a cobalt-60 source.

It may be readily appreciated that the coating may be used with good results on absorbable monofilament and multifilament sutures and ligatures as well as on nonabsorbable monofilament and multifilament sutures and ligatures.

Nonabsorbable sutures and ligatures such as cotton, linen, silk, polypropylene, and polyester are sometimes coated with nonabsorbable compositions. Polyolefins are usually of monofilament construction while cotton, linen, silk, and polyester are usually of braided, twisted, or covered multifilament construction. While there is usually no requirement that coatings on such sutures be absorbable, the composition of the invention may, nevertheless, be used as a finish for nonabsorbable sutures if desired. The only suture material that has been tried and found not to be improved by the invention is unscoured nylon monofilament. That is because unscoured nylon already has such good tie-down properties that any improvement that might be imparted by the invention is

TABLE I

| Monofilament | | % Add-on, 10 six foot strands | Smoothness of Tie-Down Ratings Based on 0–10 Subjective Scale | | | | | |
|---|---|---|---|---|---|---|---|---|
| | | | Dry | | | Wet | | |
| | | | Unsterilized/Sterilized | | | Unsterilized/Sterilized | | |
| Size 0, dyed poly-p-dioxanone monofilament | Uncoated control | | 3.5 | 4 | (EO) | 7.5 | 7.5 | (EO) |
| Size 0, dyed poly-p-dioxanone monofilament | Calcium stearate | 0.041 | 10 | 10 | " | 10 | 10 | " |
| Size 0, dyed poly-p-dioxanone monofilament | Calcium palmitate | | 10 | 9.5 | " | 9.5 | 9.5 | " |
| Size 0, dyed poly-p-dioxanone monofilament | Calcium laurate | | 10 | 10 | " | 10 | 10 | " |
| Size 0, dyed poly-p-dioxanone monofilament | Calcium oleate | | 3 | 3 | " | 8 | 8 | " |
| Size 0, dyed poly-p-dioxanone monofilament | Calcium undecylenate | | 10 | 10 | " | 9.5 | 9.5 | " |
| Size 0, dyed poly-p-dioxanone monofilament | Zinc stearate | 0.15 | 9 | 9.5 | " | 9.5 | 9 | " |
| Size 0, dyed poly-p-dioxanone monofilament | Magnesium stearate | | 10 | 10 | " | 9 | 9.5 | " |
| Size 0, dyed poly-p-dioxanone monofilament | Magnesium myristate | | 9.5 | 9.5 | " | 9.5 | 9.5 | " |
| Size 0, dyed poly-p-dioxanone monofilament | Zinc undecylate | | 10 | 10 | " | 9.5 | 10 | " |
| Size 0, dyed poly[tetramethylene terephthalate-CO—(2-octadecenyl) succinate] monofilament (U.S. Pat. No. 4,388,296) | Uncoated control | | 2 | 1.5 | (COBALT) | 2 | 2 | (COBALT) |
| | Calcium stearate | | 9 | 8 | " | 9 | 9 | " |
| | Calcium palmitate | | 8 | 8 | " | 9 | 8.5 | " |
| | Calcium laurate | | 6 | 5.5 | " | 2.5 | 4 | " |
| | Zinc stearate | | 8.5 | 8.5 | " | 8.5 | 9 | " |
| Size 0 Dyed Polypropylene monofilament | Uncoated control | | 2 | 1.5 | (EO) | 2 | 2 | (EO) |
| Size 0 Dyed Polypropylene monofilament | Calcium stearate | 0.06 | 9 | 9 | " | 9.5 | 9.5 | " |
| Size 0 Dyed Polypropylene monofilament | Calcium palmitate | | 9 | 9 | " | 9 | 9 | " |
| Size 0 Dyed Polypropylene monofilament | Calcium laurate | | 9.5 | 9.5 | " | 9.5 | 9 | " |
| Size 0 Dyed Polypropylene monofilament | Zinc stearate | 0.126 | 9.5 | 9.5 | " | 9 | 9 | " |
| Size 2/0 scoured nylon[1] monofilament | Uncoated Control | | 6.5 | — | | 7 | — | |
| | Calcium stearate | — | 10 | — | | 9.5 | — | |

[1]Soaked in acetone for 3 hours at room temperature.

As is apparent from the above results, the dry coating of the invention is effective for improving the tie-down characteristics of a variety of surgical filaments such as sutures and ligatures using various salts of fatty acids. In the tests reported in Table I, only the calcium oleate coating of the poly-(p-dioxanone) monofilament suture showed no improvement in the dry test. Even this suture showed slight improvement in the wet tie-down test, although the results were not as good as for the other salts.

not detectable by the semi-quantitative subjective test used.

EXAMPLE 3

Twenty strands of size 0 undyed polyester (polyethylene terephthalate) braid, in three-foot lengths, were coated with dry calcium stearate powder by the procedure described in Example 1, above. The add-on level for the twenty strands was 1.5 weight percent (this was probably much higher than the add-on would be in a commercial process, with a more efficient cleaning operation after the coating). Wet tie-down was 8½ (average of 4 strands), while the dry tie-down was 9 (average of 4 strands), using the same test for smoothness of tie-down described above. The uncoated controls were rated at 1 for both dry and wet. The appearance of the coated strands was excellent; they appeared to the naked eye to be uncoated.

What is claimed is:

1. A synthetic surgical filament having improved and substantially equal dry and wet tie-down properties, said surgical filament having been coated with from about 0.02 to 0.25 percent by weight of a composition consisting essentially of a dry, powdered, substantially water-insoluble, absorbable salt of a $C_6$ or higher fatty acid.

2. A surgical filament of claim 1, wherein said higher fatty acid is selected from the group consisting of $C_{12}$ to $C_{22}$ fatty acids and mixtures thereof.

3. A surgical filament of claim 1, wherein the fatty acid salt is a salt of calcium, magnesium, barium, aluminum, or zinc.

4. A surgical filament of claim 2, wherein the fatty acid salt is a salt of calcium or magnesium.

5. A surgical filament of claim 4, wherein the fatty acid comprises a mixture of stearic and palmitic acid.

6. A surgical filament of claim 5, wherein the fatty acid salt comprises a mixture of calcium palmitate and calcium stearate.

7. A surgical filament of claim 1, coated with from about 0.02 to 0.15 percent of the said mixture.

8. A surgical filament of claim 1, which is comprised of homopolymers or copolymers of lactide or glycolide.

9. A surgical filament of claim 8, wherein said surgical filament is comprised of a copolymer of 10 weight percent lactide and 90 weight percent glycolide.

10. A surgical filament of claim 9, which is a braided multifilament suture or ligature.

11. A surgical filament of claim 1, which comprises a homopolymer or a copolymer of p-dioxanone.

12. A surgical filament of claim 1, which is a monofilament suture or ligature.

13. A surgical filament of claim 11, which is a monofilament suture or ligature.

14. A surgical filament of claim 1 which is composed of a polymer selected from the group consisting of the polyolefins and the polyesters.

15. A method for imparting improving and substantially equal dry and wet tiedown properties to a surgical filament which comprises applying to the surface of said surgical filament in the form of a dry powder a water-insoluble, absorbable salt of a $C_6$ or higher fatty acid, and thereafter removing from the surface of said surgical filament excess said powder by rubbing said surface in intimate contact with a relatively powder free, non-abrasive surface until no powder is visible to the naked eye on said surgical filament surface.

16. The method of claim 15, wherein the fatty acid salt is the salt of calcium, magnesium, barium, aluminum, or zinc.

17. The method of claim 16, wherein said higher fatty acid is selected from the group consisting of $C_{12}$ to $C_{22}$ fatty acids and mixtures thereof.

18. The method of claim 15, wherein said surgical filament is an absorbable synthetic polymer selected from the group consisting of homopolymers and copolymers of lactide or glycolide.

19. The method of claim 15, wherein said surgical filament is a nonabsorbable synthetic polymer selected from the group consisting of the polyolefins and the polyesters.

20. The method of claim 16 wherein said surgical filament is a homopolymer or a copolymer of p-dioxanone.

* * * * *